United States Patent
Aharon

(10) Patent No.: US 7,893,938 B2
(45) Date of Patent: Feb. 22, 2011

(54) RENDERING ANATOMICAL STRUCTURES WITH THEIR NEARBY SURROUNDING AREA

(75) Inventor: Shmuel Aharon, West Windsor, NJ (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 1332 days.

(21) Appl. No.: 11/414,892

(22) Filed: May 1, 2006

(65) Prior Publication Data
US 2006/0253021 A1 Nov. 9, 2006

Related U.S. Application Data

(60) Provisional application No. 60/677,791, filed on May 4, 2005.

(51) Int. Cl.
G06T 15/40 (2006.01)
G06T 15/00 (2006.01)
G06T 17/20 (2006.01)
G06T 15/50 (2006.01)
G06T 17/00 (2006.01)
G09G 5/02 (2006.01)
G06K 9/00 (2006.01)

(52) U.S. Cl. ............... 345/422; 345/419; 345/423; 345/426; 345/619; 345/629; 382/130; 382/131; 382/132

(58) Field of Classification Search ............... 345/419, 345/422, 423, 426, 619, 629; 382/130–132; 434/267, 272
See application file for complete search history.

(56) References Cited

U.S. PATENT DOCUMENTS

| | | | | |
|---|---|---|---|---|
| 5,222,202 A * | 6/1993 | Koyamada | | 345/423 |
| 5,239,591 A * | 8/1993 | Ranganath | | 382/128 |
| 5,452,407 A * | 9/1995 | Crook | | 345/421 |
| 5,568,384 A * | 10/1996 | Robb et al. | | 715/202 |
| 5,793,375 A * | 8/1998 | Tanaka | | 345/426 |
| 5,798,764 A * | 8/1998 | Akiyama | | 345/423 |
| 5,825,908 A * | 10/1998 | Pieper et al. | | 382/131 |
| 5,839,440 A * | 11/1998 | Liou et al. | | 600/431 |
| 5,920,319 A * | 7/1999 | Vining et al. | | 345/420 |
| 5,926,568 A * | 7/1999 | Chaney et al. | | 382/217 |
| 5,971,767 A * | 10/1999 | Kaufman et al. | | 434/267 |
| 5,986,662 A * | 11/1999 | Argiro et al. | | 345/424 |
| 6,061,469 A * | 5/2000 | Walterman | | 382/154 |

(Continued)

OTHER PUBLICATIONS

G. Glombitza, W. Lamade, A. M. Demiris, and C. Herfarth, et al., "Virtual planning of liver resections: Image processing, visualization and volumetric evaluation", International Journal of Medical Informatics, vol. 53, Issues 2-3, pp. 225-237.*

(Continued)

*Primary Examiner*—Ulka Chauhan
*Assistant Examiner*—Roberta Prendergast
(74) *Attorney, Agent, or Firm*—Donald B. Paschburg; F. Chau & Associates, LLC

(57) ABSTRACT

System and methods of displaying anatomical structures and their surrounding area, are disclosed. For a viewing point the anatomical structures are rendered separate from their surrounding and saved. The surrounding area of the anatomical structure within a viewing frustum is extracted, interpolated and rendered. The rendered anatomical structures and calculated image of the surrounding are combined into a complete rendering of the anatomical structures with its nearby surrounding areas.

15 Claims, 6 Drawing Sheets

U.S. PATENT DOCUMENTS 6,310,620 B1 * 10/2001 Lauer et al. ............... 345/424
6,876,362 B1 * 4/2005 Newhall et al. ............ 345/426

OTHER PUBLICATIONS

Hauser, H., Mroz, L., Bischi, G., and Gröller, M. E., "Two-level volume rendering—fusing MIP and DVR", Proceedings of the Conference on Visualization '00, Jul. 2000, IEEE Visualization, IEEE Computer Society Press, Los Alamitos, CA, pp. 211-218.*

Sun et al., "Recent Development on Computer-Aided Tissue Engineering- A Review", Computer Methods and Programs in Biomedicine, vol. 67, Issue 2, Feb. 2002, pp. 85-103.*

Vetter, et al., "Superiority of autostereoscopic visualization for image-guided navigation in liver surgery", Proceedings SPIE vol. 4681—Medical Imaging 2002: Visualization, Image-Guided Procedures, and Display, pp. 196-203, May 2002.*

Viola, I., Kanitsar, A., and Groller, M. E., "Importance-Driven Volume Rendering", Proceedings of the Conference on Visualization '04, Oct. 10-15, 2004, IEEE Visualization, IEEE Computer Society, Washington, DC, pp. 139-146.*

W. C. K. Wong, A. C. S. Chung, and S. C. H. Yu, "Local orientation smoothness prior for vascular segmentation of angiography", 2003, Submitted to ECCV 2004, Proceedings of the European Conference on Computer Graphics, May 11-14, 2004, pp. 353-365.*

Wu, et al., "Shear-image order ray casting volume rendering", Proceedings of the 2003 Symposium on interactive 3D Graphics, Monterey, California, Apr. 27-30, 2003, I3D '03, ACM, New York, NY, pp. 152-162.*

Etienne, Alex, et al, ""Soap-Bubble" Visualization and Quantitative Analysis of 3D Coronary Magnetic Resonance Angiograms," Magnetic Resonance in Medicine 48: 658-666, 2002.

Tuchschmid, Stefan, "Coroviz: Visualization of 3D Whole-Heart Coronary Artery MRA Data," Master's Thesis: Swiss Federal Institute of Technology Zurich Switzerland, 2004.

Tuchschmid, Stefan, et al., "Coroviz: Visualization of 3D Whole-Heart Coronary Artery MRA Data," ISMRM 13. Scientific Meeting, May 2005.

Weber, Oliver, et al., "Whole-Heart Steady-State Free Precession Coronary Artery Magnetic Resonance Angiography," Magnetic Resonance in Medicine 50: 1223-1228, 2003.

* cited by examiner

RENDERING ANATOMICAL STRUCTURES WITH THEIR NEARBY SURROUNDING AREA

CROSS-REFERENCE TO RELATED APPLICATIONS

This application claims the benefit of U.S. Provisional Patent Application No. 60/677,791, filed May 4, 2005, which is incorporated herein by reference.

BACKGROUND OF THE INVENTION

The present invention relates to the visualization of anatomical structures and more particularly to the visualization of structures with their nearby surrounding area visible.

The rendering of anatomical structures, such as organs, is an important visualization tool for many medical applications. These medical applications include surgical planning, noninvasive diagnosis, and image-guided surgery.

The anatomical structures can be rendered directly using an appropriate transfer function, from a previously calculated segmentation mask, or from a pre-generated surface (polygonal mesh). All of these rendering techniques provide detailed visualization of the anatomical structure but completely masks out of the image the area surrounding these structures. This lack of surrounding area information significantly reduces the effectiveness of the visualization, and makes it very difficult to identify the exact location and orientation of the visualized structures. For example, one can render the coronaries tree branches. However, if only the coronaries trees are visible it becomes very difficult to distinguish between the left and right side, or where is up and down. It becomes very important to render the coronaries tree together with their surrounding area context. By being able to visualize coronaries nearby surrounding structures such as, the heart chambers and muscles, one can identify correctly the coronaries orientation and location in the body.

Straightforward rendering of anatomical structures and their nearby surrounding is not possible without significant visualization artifacts. For example, one can render the anatomical structure and then render the entire volume excluding the areas covered by the anatomical structure. Although, this will provide some surrounding area information it will cause many problems and artifacts. First, rendering the entire volume will display information from areas located far from the anatomical structure of interest, masking out important nearby information. Second, combining in an image rendering from areas of different distances from the observer (depth) will cause aliasing artifacts on the image.

Accordingly novel rendering methods are required that will provide nearby surrounding area rendering together with the anatomical structures of interest without any artifacts or masking of nearby information.

SUMMARY OF THE INVENTION

One aspect of the present invention presents a novel rendering technique and system that will provide nearby surrounding area rendering together with the anatomical structures without any artifacts or masking of nearby information. The implementation can be done using the OpenGL or DirectX APIs.

In accordance with a further aspect of the present invention a method is provided of processing medical image data for smooth rendering from a defined point of view of one or more anatomical structures with a nearby surrounding area from 3D image data, wherein the one or more anatomical structures are separated from the nearby surrounding area, comprising: creating an image by rendering the one or more separated anatomical structures from the defined point of view and saving a depth information of the rendered anatomical structures and saving the rendered image of the anatomical structures; extracting a boundary between the rendered one or more anatomical structures and the nearby surrounding area using the depth information of the rendered anatomical structures; rendering the nearby surrounding area from the defined point of view; and combining the renderings of the anatomical structures and the nearby surrounding area.

In accordance with another aspect of the present invention a method is provided wherein corresponding near-plane depth information of the rendered anatomical structures will be saved as a first Z-buffer with non-visible pixels set to value 1.

In accordance with a further aspect of the present invention a method is provided wherein rendering the nearby surrounding area includes: extracting from the first Z-buffer all the pixels that lie on a boundary between visible and non-visible area; storing each boundary pixel's image coordinates in a 2D array; adding four points to the 2D array as defined by the visualization frustum; creating a 2D mesh as defined by the 2D array points; and projecting the 2D mesh to a 3D mesh by assigning to each point defining the 2D mesh its corresponding 3D coordinate.

In accordance with another aspect of the present invention a method is provided wherein rendering the nearby surrounding area further includes interpolating points on the 3D mesh to determine pixels in the nearby surrounding area.

In accordance with a further aspect of the present invention a method is provided wherein the 2D mesh is created by applying Delaunay triangulation.

In accordance with another aspect of the present invention a method is provided wherein a second near-plane depth information is created comprising: rendering the 3D mesh and saving the corresponding near-plane depth information of the rendered mesh as a second Z-buffer with non-visible pixels set to value 1; and setting the pixels that corresponds to visible pixels in the first Z-buffer to value 0.

In accordance with a further aspect of the present invention a method is provided wherein the anatomical structures are rendered with the nearby surrounding area from 3D image data comprising: creating an image by rendering the 3D image data using the second Z-buffer as the rendering rays entry points into the data; propagating the rays a specified depth distance into the data; skipping the pixels with second Z-buffer values of one; and assigning to each pixel with second Z-buffer values of zero the corresponding value from the saved rendered anatomical structure.

In accordance with another aspect of the present invention a method is provided wherein far-plane depth information is used for determining the rendering rays exit points from the data.

In accordance with a further aspect of the present invention, a system including a processor and software operable on the processor to perform the previously stated tasks and methods is provided.

These steps can also be performed in a system with a graphics processing unit.

DESCRIPTION OF A PREFERRED EMBODIMENT

In order to illustrate the different aspects of the present invention, the rendering of blood vessels in the heart and more specifically the left and right coronary arteries in their nearby surroundings will be used. The issue of rendering of coronary arteries within the context of surrounding anatomical structures without distortion, masking or introducing visualization artifacts is known. In the following, a three-dimensional image data set, as obtained from known medical-imaging equipment, is worked upon to present to a user a visually useful image corresponding to the image data set. In particular, blood vessels with their surrounding contextual information may be displayed. The image data set may be obtained, for example, from whole heart magnetic resonance angiography (MRA). It will be appreciated that three-dimensional data sets obtained by other means may also be utilized. That is, the present invention is not limited to specific types of three-dimensional datasets, file formats, voxel or pixel resolutions, or the like. The three dimensional data set may be thought of as describing a plurality of specific locations in space, each with a corresponding intensity value.

Figure 1:
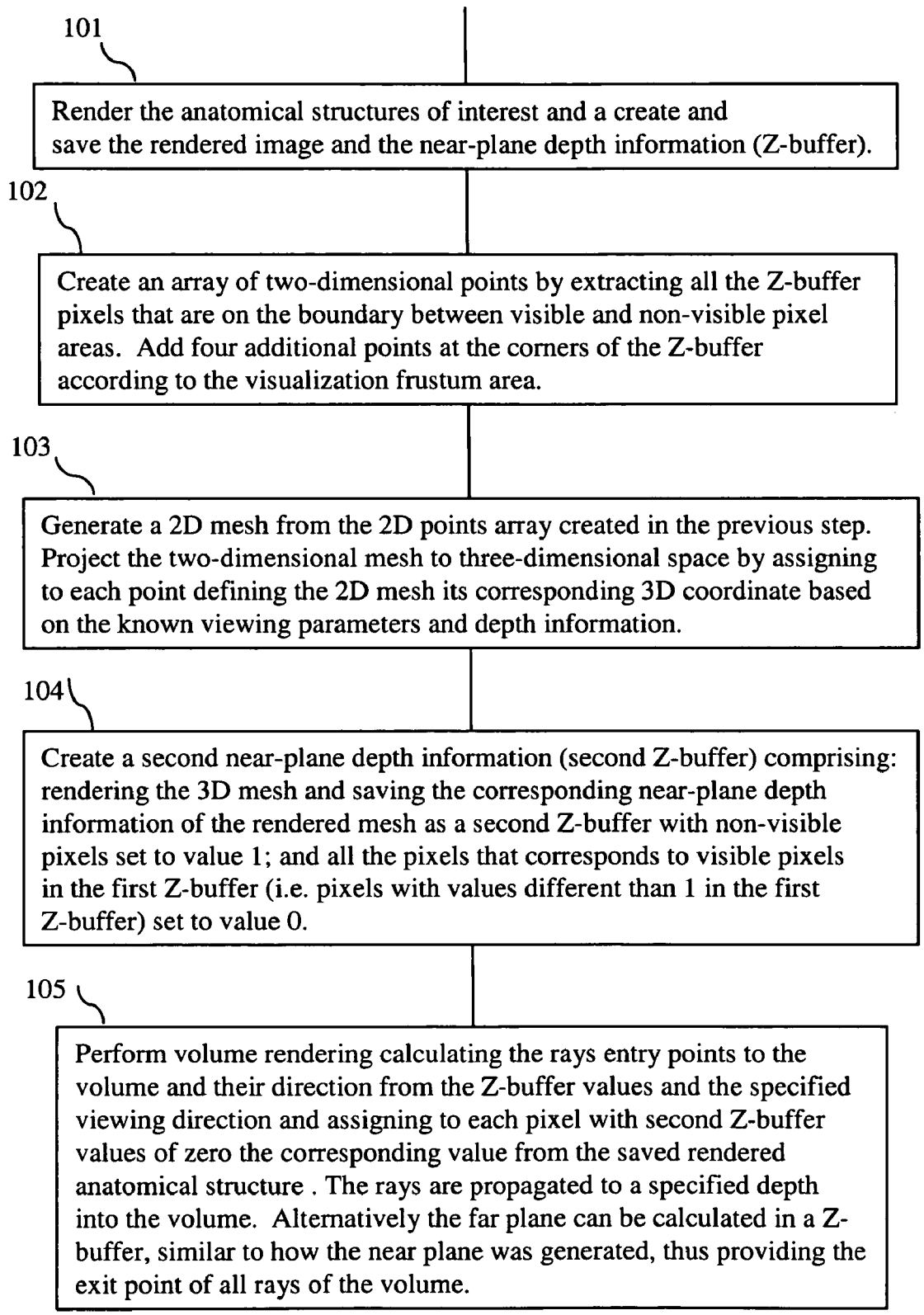
FIG. 1 is a flow diagram showing steps of the method in the present invention.

In accordance with one aspect of the present invention, a rendering method includes 5 steps which will next be described and illustrated. The steps are also presented in a flow diagram in FIG. 1.

In step 101, the anatomical structures of interest in the data volume are rendered using a preferred rendering technique. For example the Maximum Intensity Projection (MIP) rendering technique can be used.

Figure 2:
FIG. 2 shows a rendered image of coronary arteries without surrounding area.
Figure 3:
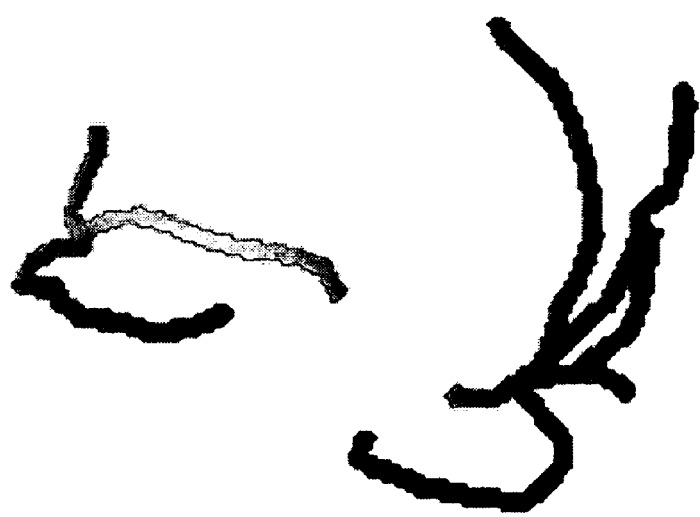
FIG. 3 shows the near-plane depth information (Z-buffer) of the rendered coronary arteries.

During the rendering of step 101, the distance of every voxel that is displayed on the rendered image from the viewing point (camera) is stored in the Z-buffer. This provides the depth of the near plane for each visible pixel on the rendered image. Non-visible pixels will set to the value of 1. This is shown in FIG. 2, wherein the coronary arteries are rendered and displayed without any information about their surrounding anatomical structures. In case of blending operations, when more than one voxel contributes to the output image, the distance to the nearest contributing voxel is stored. The results are a detailed rendering of the anatomical structures and the corresponding near-plane Z-buffer. These rendering results are saved for later use. This is shown in FIG. 3, wherein the depth from a defined point of view is depicted as a shade of grey.

Step 102 will now be described. The Z-buffer, from step 101, is processed to extract all the pixels that lie on the boundary between visible and none-visible areas. This can be done, by checking the neighboring pixels of a given pixel. If all of these neighboring pixels are either all visible or all non-visible, this pixel is ignored. Otherwise, this pixel is a boundary pixel and its image coordinates are stored in a two-dimensional (2D) point's array.

An additional four points are added based on a bounding box defining the part of the data one would like to visualize. This bounding box is also known as the visualization frustum. These points are usually added somewhere close to the corners of the Z-buffer image.

Figure 4:
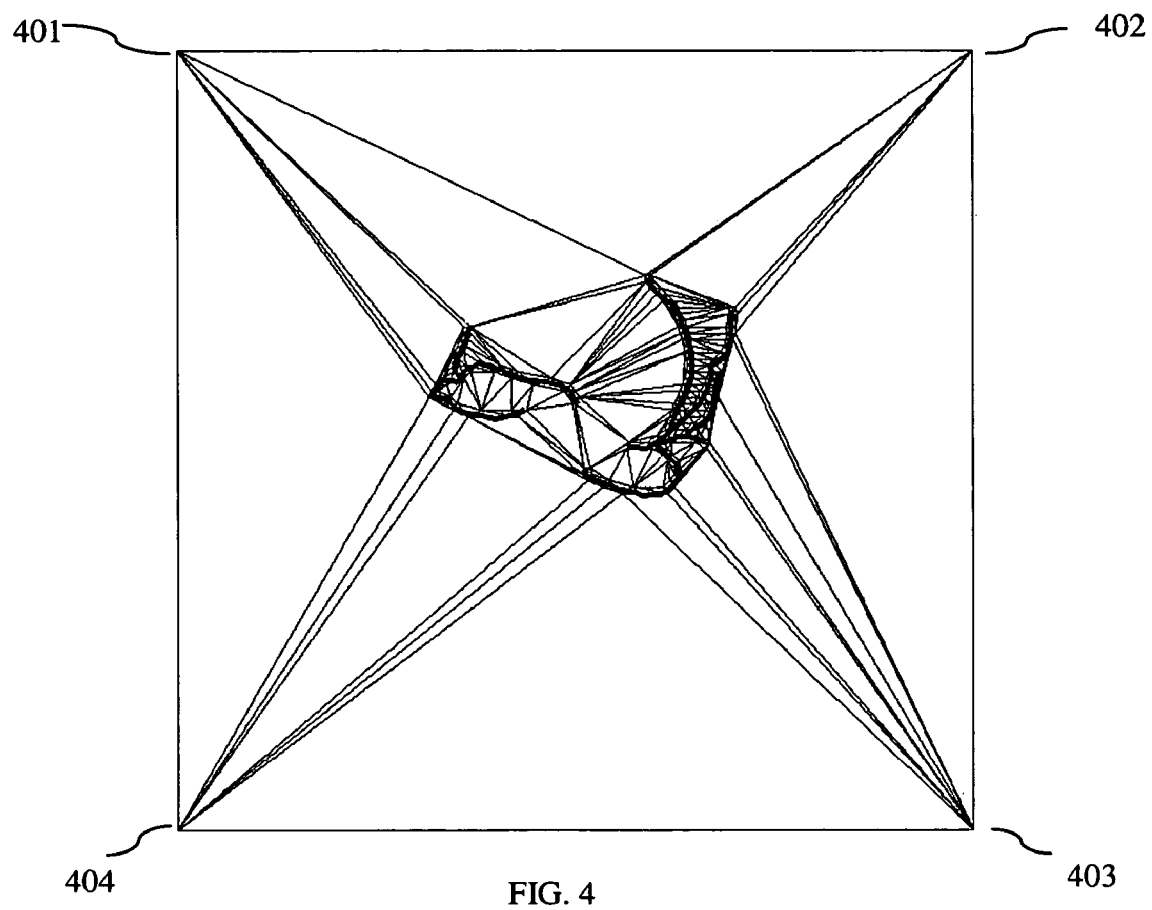
FIG. 4 shows the Delaunay triangular mesh representing the surrounding area of the coronary arteries.
Figure 5:
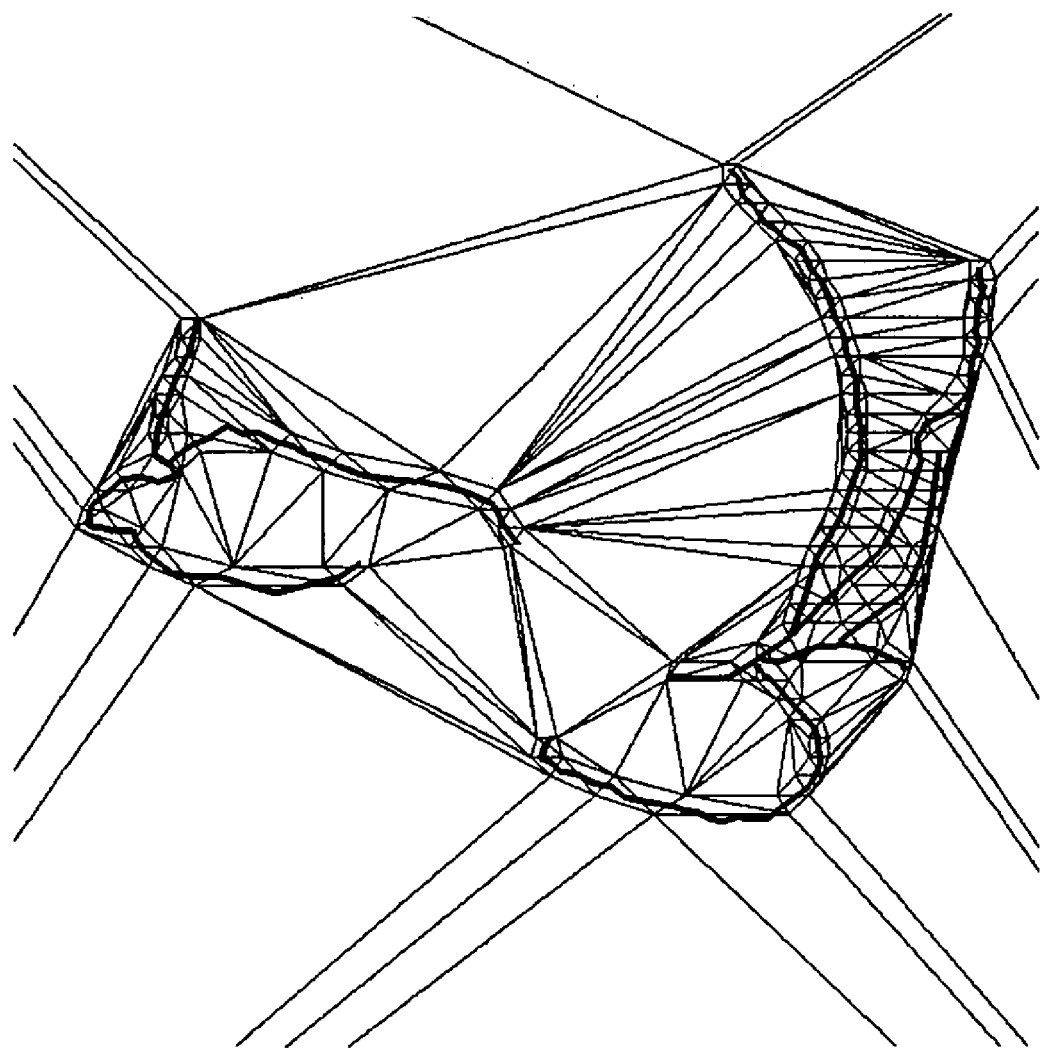
FIG. 5 shows details of a Delaunay triangular mesh.

Step 103 will now be described. A 2D mesh is then generated, from the point's array generated in step 102. The 2D mesh can be generated using Delaunay triangulation. This is illustrated in FIG. 4 which shows the Delaunay triangles within the bounding box with borders 401, 402, 403 and 404. The triangulation is shown in further detail in FIG. 5. The mesh is then projected back into three-dimension (3D) by adding to every point its 3D coordinate calculated from its corresponding depth value in the Z-buffer and the given viewing direction/position.

Step 104 will now be described. The Z-buffer is now set for the next rendering step as follows. The values of all the pixels that correspond to visible pixels in the Z-buffer from step 101 (pixels with Z-buffer value less than 1) are set to zero. Other pixels are set to the value of one. Using this generated Z-buffer, the 3D triangular mesh, generated in step 103, is then rendered using the "less than" depth function and the newly generated Z-buffer is saved. This will result a Z buffer with values that are linearly interpolated to have a smooth change in depth between the edges of the visible parts of the anatomical structures to some given depth in its surrounding area.

Step 105 will now be described. The volume is now rendered into the rendered image that was saved in step 101, using a given rendering algorithm. The Z-buffer values from step 104 provide the entry points to the volume data. Pixels with Z-buffer values that equal to zero are skipped since they correspond to visible parts of the rendered anatomical structures, which are already defined in the rendered image (from step 101). The rays are propagated some specified depth into the volume. The result is a complete rendering of the anatomical structures with their surrounding area smoothly filled around their none-visible parts without image artifacts. Alternatively, the far plane can be calculated in a Z-buffer, similar to how the near plane was generated and this will provide the exit point of all rays from the volume.

Figure 6:
FIG. 6 shows the projected arteries (LCA and RCA) in one image within the rendered context of their surrounding area.

The end result is illustrated in FIG. 6 which shows the distortion free projection of the two coronary artery trees 601 and 602 in the context of the surrounding anatomical 603 structures of the heart.

Figure 7:
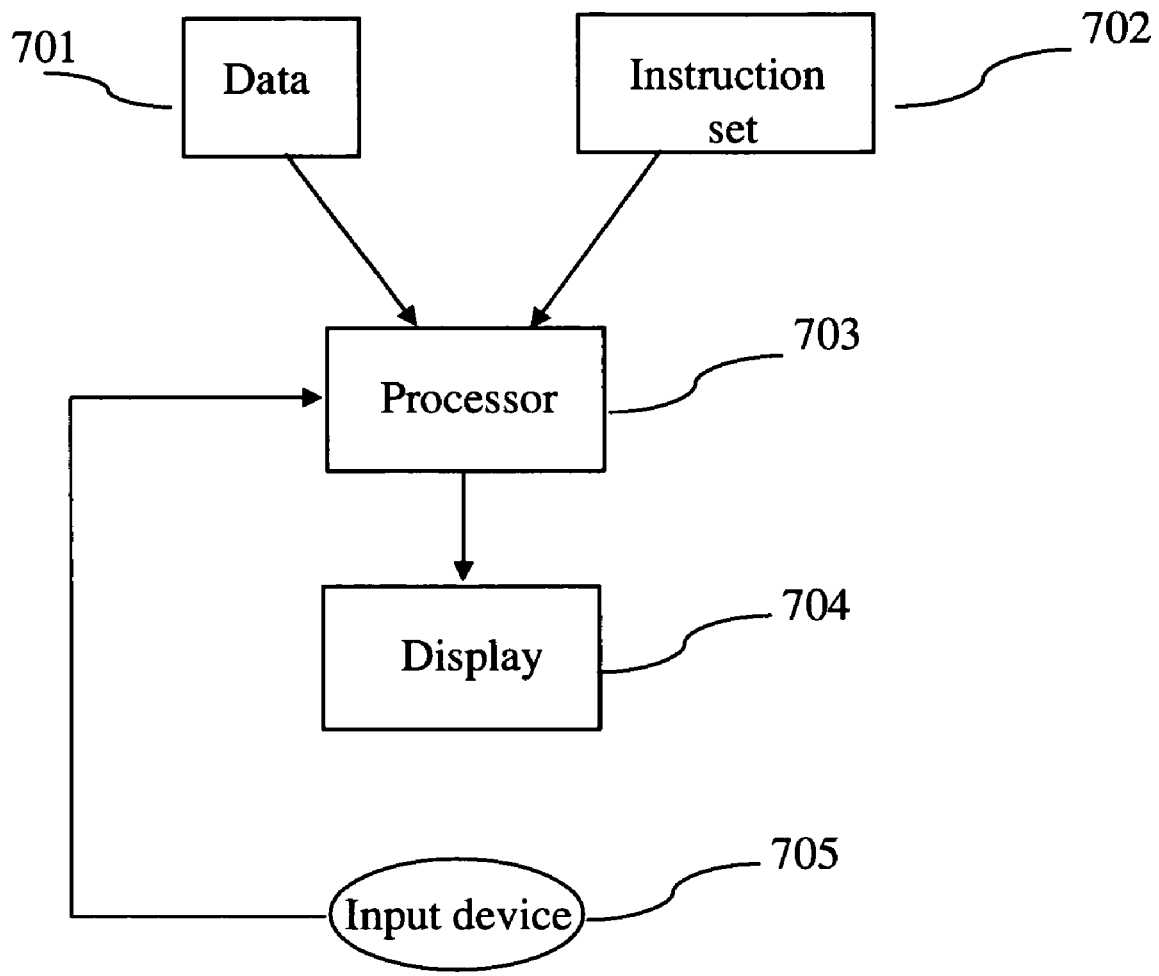
FIG. 7 shows a diagram of a system according to the present invention.

FIG. 7 illustrates a computer system that can be used in accordance with one aspect of the present invention. The system is provided with data 701 representing the to be displayed image. An instruction set or program 702 comprising the methods of the present invention is provided and combined with the data in a processor 703, which can process the instructions of 702 applied to the data 701 and show the resulting image on a display 704. The instructions 702 may also comprise the instructions to extract anatomical structure of interest from the volume data. The processor can be dedicated hardware, a GPU, a CPU or any other computing device that can execute the instructions of 702. An input device 705 like a mouse, or track-ball or other input device allows a user to select for instance the viewing direction and to start the displaying process. Consequently the system as shown in FIG. 7 provides an interactive system for rendering anatomical structures with their nearby surrounding area.

In this disclosure, the term "pixel" is used to indicate a data structure that is used to compose an image. Although the term typically indicates a two-dimensional element, for purposes of the following disclosure, "pixel" is also intended to include three-dimensional picture elements, i.e., voxels.

While there have been shown, described and pointed out fundamental novel features of the invention as applied to preferred embodiments thereof, it will be understood that various omissions and substitutions and changes in the form and details of the device illustrated and in its operation may be made by those skilled in the art without departing from the spirit of the invention. It is the intention, therefore, to be limited only as indicated by the scope of the claims appended hereto.

The invention claimed is:

1. A method of processing medical image data for smooth rendering from a defined point of view of one or more anatomical structures with a nearby surrounding area from 3D image data, wherein the one or more anatomical structures are separated from the nearby surrounding area, comprising:

creating an image by rendering with a processor the one or more separated anatomical structures from the defined point of view and saving a depth information of the rendered anatomical structures in a first Z-buffer with non-visible pixels set to value 1 and saving the rendered image of the anatomical structures;

extracting a boundary between the rendered one or more anatomical structures and the nearby surrounding area using the depth information of the rendered one or more anatomical structures;

rendering the nearby surrounding area from the defined point of view, including the steps of extracting from the first Z-buffer the pixels that lie on a boundary between visible and non-visible areas, storing each boundary pixel's image coordinates in a 2D array, adding four points to the 2D array as defined by a visualization frustum; creating a 2D mesh as defined by the 2D array points; and projecting the 2D mesh to a 3D mesh by assigning to each point defining the 2D mesh its corresponding 3D coordinate, and combining the renderings of the one or more anatomical structures and the nearby surrounding area to be displayed on a display.

2. The method as claimed in claim 1, wherein rendering the nearby surrounding area further includes interpolating points on the 3D mesh to determine pixels in the nearby surrounding area.

3. The method as claimed in claim 1, wherein rendering the nearby surrounding area further includes interpolating coordinates of points on the 3D mesh and accessing the medical image data based on the coordinates to determine pixels in the nearby surrounding area.

4. The method as claimed in claim 1, wherein the 2D mesh is created by applying Delaunay triangulation.

5. The method as claimed in claim 1, wherein second near-plane depth information is created, comprising the steps:

rendering the 3D mesh and saving the corresponding near-plane depth information of the rendered mesh as a second Z-buffer with non-visible pixels set to value 1; and setting the pixels that corresponds to visible pixels in the first Z-buffer to value 0.

6. The method as claimed in claim 5, wherein the one or more anatomical structures are rendered with the nearby surrounding area from 3D image data comprising:

creating an image by rendering the 3D image data using the second Z-buffer as the rendering rays entry points into the data;

propagating the rays a specified depth distance into the data;

skipping the pixels with second Z-buffer values of one; and assigning to each pixel with second Z-buffer values of zero the corresponding value from the saved rendered one or more anatomical structures.

7. The method as claimed in claim 1, wherein far-plane depth information is used for determining the rendering rays exit points from the data.

8. A system of processing medical image data for smooth rendering from a defined point of view of one or more anatomical structures with a nearby surrounding area from 3D image data, wherein the one or more anatomical structures are separated from the nearby surrounding area, comprising:

a processor;

software operable on the processor for:

creating an image by rendering the one or more separated anatomical structures from the defined point of view and saving a depth information of the rendered one or more anatomical structures in a first Z-buffer with non-visible pixels set to value 1 and saving the rendered image of the one or more anatomical structures;

extracting a boundary between the rendered one or more anatomical structures and the nearby surrounding area using the depth information of the rendered one or more anatomical structures;

rendering the nearby surrounding area from the defined point of view, including extracting from the first Z-buffer the pixels that lie on a boundary between visible and non-visible areas, storing each boundary pixel's image coordinates in a 2D array, adding four points to the 2D array as defined by a visualization frustum; creating a 2D mesh as defined by the 2D array points; and projecting the 2D mesh to a 3D mesh by assigning to each point defining the 2D mesh its corresponding 3D coordinate, and combining the renderings of the one or more anatomical structures and the nearby surrounding area.

9. The system as claimed in claim 8, wherein rendering the nearby surrounding area further includes interpolating points on the 3D mesh to determine pixels in the nearby surrounding area.

10. The system as claimed in claim 8, wherein rendering the nearby surrounding area further includes interpolating coordinates of points on the 3D mesh and accessing the medical image data based on the coordinates to determine pixels in the nearby surrounding area.

11. The system as claimed in claim 8, wherein the 2D mesh is created by applying Delaunay triangulation.

12. The system as claimed in claim 8, wherein second near-plane depth information is created comprising:

rendering the 3D mesh and saving the corresponding near-plane depth information of the rendered mesh as a second Z-buffer with non-visible pixels set to value 1; and setting the pixels that corresponds to visible pixels in the first Z-buffer to value 0.

13. The system as claimed in claim 12, wherein the one or more anatomical structures are rendered with the nearby surrounding area from 3D image data comprising:

creating an image by rendering the 3D image data using the second Z-buffer as the rendering rays entry points into the data;

propagating the rays a specified depth distance into the data;

skipping the pixels with second Z-buffer values of one; and assigning to each pixel with second Z-buffer values of zero the corresponding value from the saved rendered one or more anatomical structures.

14. The system as claimed in claim 8, wherein far-plane depth information is used for determining the rendering rays exit points from the data.

15. The system as claimed in claim 8, wherein the processor is a graphics processing unit.

* * * * *